United States Patent [19]

Dowd et al.

[11] 4,144,265

[45] Mar. 13, 1979

[54] PROCESS FOR THE MANUFACTURE OF M-TRIFLUOROMETHYL BENZYL NITRILE

[75] Inventors: William Dowd; Thomas H. Fisher, both of Midland, Mich.

[73] Assignee: The Dow Chemical Company, Midland, Mich.

[21] Appl. No.: 925,336

[22] Filed: Jul. 17, 1978

[51] Int. Cl.$^2$ .................. C07C 120/04; C07C 121/66
[52] U.S. Cl. ................................................ 260/465 G
[58] Field of Search ........................ 260/465 G, 465 R

[56] References Cited

U.S. PATENT DOCUMENTS

| | | | |
|---|---|---|---|
| 3,573,032 | 3/1971 | Fellig et al. | 71/105 |
| 3,992,432 | 11/1976 | Napier et al. | 260/465.1 |
| 4,056,509 | 11/1977 | Verbrugge et al. | 260/465 G |

OTHER PUBLICATIONS

Hennis et al., I&EC Product Research and Development, vol. 7, pp. 96–101 (1968).
Yadav, Chemical Industry Developments, p. 21 (1975).
Dehmlow, Chem. Tech., p. 216 (1975).
Reeves et al., Synthetic Communications, vol 6., No. 3, pp. 193–197 (1976).
Weber et al., Phase Transfer Catalysis in Organic Synthesis, pp. 98–101 (1977).

*Primary Examiner*—Dolph H. Torrence
*Attorney, Agent, or Firm*—Lester J. Dankert; Joyce P. Hill

[57] ABSTRACT

Quaternary ammonium salts, such as methyl tributyl ammonium chloride, are novel catalysts in a nitrile-forming reaction which comprises stirring together aqueous sodium cyanide and the undistilled m-trifluoromethyl benzyl chloride product of the reaction of chloromethyl methyl ether, chlorosulfonic acid and trifluoromethyl benzene from which chloromethyl ether impurities, methanol, water and some of the unreacted trifluoromethyl benzene are removed. The process is conducted under alkaline conditions in a two-phase liquid reaction medium. m-Trifluoromethyl benzyl nitrile is prepared in excellent yields and purity.

7 Claims, No Drawings

PROCESS FOR THE MANUFACTURE OF M-TRIFLUOROMETHYL BENZYL NITRILE

BACKGROUND OF THE INVENTION m-Trifluoromethyl benzyl nitrile is described by Fellig et al. in U.S. Pat. No. 3,573,032 as a useful intermediate for herbicidal compositions. m-Trifluoromethyl benzyl nitrile is represented by formula (I).

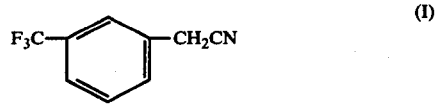
(I)

Fellig et al. disclosed the preparation of (I) by reacting sodium cyanide and the appropriate benzyl chloride in aqueous acetone, dimethylformamide (DMF) or dimethylsulfoxide (DMSO) as a reaction medium. In aqueous acetone, the reaction proceeds very slowly. In DMF, a 40 to 50 percent yield is obtained in about 5 hours at from 60° C. to 70° C. In DMSO, a 60 to 80 percent yield is obtained in 1 to 2 hours at 80° C. with no unreacted benzyl halide remaining. Because of the high yields and short reaction times, DMSO has heretofore been the preferred reaction medium.

Prior to this invention, anhydrous solvents were required to create a homogeneous phase that would allow the reaction between the chloride and cyanide reactants to occur. The anhydrous solvents are costly.

This invention provides an integrated, efficient process for the production of m-trifluoromethyl benzyl nitrile in high yields and purity and under mild reaction conditions as desired by those skilled in the art.

SUMMARY OF THE INVENTION m-Trifluoromethyl benzyl nitrile is prepared when aqueous sodium cyanide and a chloromethylation crude containing m-trifluoromethyl benzyl chloride are stirred together in the presence of a catalytic amount of a phase transfer catalyst, such as methyl tributyl ammonium chloride. The chloromethylation crude results from the reaction of chloromethyl methyl ether (CMME) and chlorosulfonic acid with trifluoromethyl benzene to form a reaction product from which chloromethyl ether impurities, methanol, water, and some of the unreacted trifluoromethyl benzene are removed. The chloromethylation crude, which is referred to herein alternatively as the undistilled m-trifluoromethyl benzyl chloride, is reacted with aqueous sodium cyanide under alkaline conditions, preferably in a two-phase liquid reaction medium. The use of a phase transfer catalyst represents a substantial process improvement over the prior art in that mild reaction conditions are now possible for the production of the desired m-trifluoromethyl benzyl nitrile in excellent yields and purity. In addition, simplified recovery of the desired product results from this process relative to known art.

DETAILED DESCRIPTION OF THE INVENTION

In a nitrile-forming reaction wherein undistilled m-trifluoromethyl benzyl chloride is reacted with aqueous sodium cyanide in a two-phase liquid medium, a catalytic amount of a quaternary ammonium salt is used to prepare m-trifluoromethyl benzyl nitrile under mild conditions.

The undistilled m-trifluoromethyl benzyl chloride is one of the products of the chloromethylation of trifluoromethyl benzene wherein chloromethyl methyl ether, trifluoromethyl benzene and chlorosulfonic acid are reacted in molar ratios of from 1.2:1:0.5 to 2.0:1:1. German Pat. No. 1,568,938 discloses two methods for the preparation of m-trifluoromethyl benzyl chloride: (1) Reacting the appropriate trifluoromethyl aryl with chlorosulfonic acid and para-formaldehyde in the presence of zinc chloride; (2) Reacting the appropriate trifluoromethyl aryl with chlorosulfonic acid and chloromethyl methyl ether. The disclosure of method (2) of German Pat. No. 1,568,938 is incorporated herein by reference. The chloromethylation reaction may be carried out in the range of from about 35° C. to about 65° C. When the temperature is within a range of from about 35° C. to about 40° C. the chloromethylation reaction requires 12 to 16 hours; in a higher range of from about 55° C. to about 65° C. the reaction requires from 2 to 3 hours, using the ratio of reactants specified above.

The preparation of m-trifluoromethyl benzyl chloride via the chloromethylation of trifluoromethyl benzene results in the concurrent production of undesirable chloromethyl ether impurities. The removal of the chloromethyl ether impurities is desirable and treatment with an aqueous base is preferred. U.S. Pat. No. 3,994,984 and German Pat. No. 2,620,344 specifically disclose processes for the removal of chloromethyl ether impurities from alkyl benzyl chlorides and are incorporated herein by reference. In the instant invention after the chloromethylation reaction crude is washed with water and phase-separated into an aqueous and an organic layer, bis-chloromethyl ether impurities are removed from the organic layer of the crude chloromethylation reaction product by washing with a 20 percent NaOH solution.

Following the base wash which decomposes the bis-chloromethyl ether impurities, the resulting, ether-free chloromethylation reaction crude is phase-separated into an aqueous base layer and a crude organic product layer. The crude organic product layer is charged to a flash still to remove methanol, water and part of the unreacted trifluoromethyl benzene. The remaining organic crude layer is the undistilled m-trifluoromethyl benzyl chloride used in the nitrile-forming reaction with aqueous sodium cyanide in the presence of a quaternary ammonium salt which functions as a phase transfer catalyst.

It is surprising and extremely advantageous to be able to use undistilled m-trifluoromethyl benzyl chloride. Prior to this invention it was taught that the preparation of m-trifluoromethyl benzyl nitrile required the isolation of the chloride intermediate before further treatment in a homogeneous liquid reaction medium. Isolation of the chloride intermediate is achieved by a costly, tedious distillation step with severe corrosion within the distillation columns.

The undistilled m-trifluoromethyl benzyl chloride, the organic phase, is combined with an aqueous phase containing from 5 to 40, preferably 15-21, weight percent sodium cyanide or potassium cyanide thereby creating a two-phase liquid reaction medium comprising an inert, water-immiscible, organic liquid and water. Since the undistilled m-trifluoromethyl benzyl nitrile is liquid, an additional solvent is not necessary; however, an inert organic liquid such as methylene chloride ($CH_2Cl_2$), chloroform, carbon tetrachloride, benzene, toluene, cyclohexane, and other like chlorinated hydrocarbon solvents and hydrocarbon solvents may be employed. Even though the reactants, m-trifluoromethyl benzyl chloride and the cyanide compound are in separate phases rather than in a common solvent (i.e., dimethylsulfoxide), contact between the reactants is facilitated by the addition of a phase transfer catalyst in accord with the process of this invention. With stirring the desired nitrile-forming reaction proceeds smoothly, under mild conditions and at a commercially attractive rate.

It is theorized that during the nitrile-forming reaction, sodium cyanide or potassium cyanide, well-known compounds that are extremely soluble in water, remain primarily in the aqueous phase but dissociated into ions (i.e., sodium ($Na^+$) and cyanide ($CN^-$)). In the presence of a phase transfer catalyst, the cyanide ion is transported into the organic phase and displaces the chloride ion of the m-trifluoromethyl benzyl chloride. The phase transfer catalyst then transports the chloride ion to the aqueous phase, releases the chloride ion and repeats the previous cycle. The by-product chloride is washed free from the reaction by stirring the reaction medium and is retained in the aqueous phase while the product nitrile is retained in the organic phase.

Compounds from the known class of quaternary ammonium salts are particularly suitable phase transfer catalysts in the instant invention.

Suitable quaternary ammonium salts have a minimum solubility of at least about 1 weight percent in both the organic phase and the aqueous phase of a two-phase reaction medium at 25° C. The ammonium salts can be represented by the formula $R_1R_2R_3R_4N^\oplus A^\ominus$, wherein $R_1$–$R_4$ are hydrocarbyl groups (e.g., alkyl, aryl, alkaryl, aralkyl, cycloalkyl, etc.) and $R_1$ can join with $R_2$ to form a 5- or 6-membered heterocyclic compound having at least one quaternized nitrogen atom in the ring and may also contain one atom of nitrogen, oxygen or sulfur within the ring. Typically, $R_1$–$R_4$ are hydrocarbyl groups of from 1 to about 12 carbon atoms. $A^\ominus$ is a neutralizing anion and may be varied to convenience. Chloride and bromide are the preferred anions, but other representative anions include fluoride, tosylate, acetate, bisulfate, etc. It is also possible to generate the phase transfer catalyst in situ by the addition of triethylamine to the starting reactants; m-trifluoromethyl benzyl triethyl ammonium chloride is generated via this method. Following are more compounds which are illustrative phase transfer catalysts: tetraalkyl ammonium salts, such as tetramethyl-, tetraethyl-, tetrabutyl-, tetrahexyl-, methyltriethyl-, methyltributyl-, trioctylmethyl- and tridecylmethyl- -ammonium chlorides, bromides, bisulfates, tosylates, etc.; aralkylammonium salts, such as tetrabenzylammonium chloride, benzyltrimethyl-, benzyltriethyl-, benzyltributyl-, and phenethyltrimethyl ammonium chlorides, bromides, etc., arylammonium salts, such as triphenylmethylammonium fluoride, chloride or bromide, N,N,N-trimethylanilinium chloride, N,N,N-triethylanilinium bromide, N,N-diethyl-N-ethylanilinium bisulfate, trimethylnaphthylammonium chloride, p-methylphenyltrimethylammonium chloride or tosylate, etc.; 5- and 6-membered heterocyclic compounds containing at least one quaternized nitrogen atom in the ring, such as N,N,N',N'-tetramethylpiperazinium-dichloride, N-methylpyridinium chloride, 1-methyl-1-azoniabicyclo [2.2.1]- heptane bromide, N,N-dibutylmorpholinium chloride, N-ethylthiazolium chloride, N-butylpyrrolium chloride, etc., and other like compounds.

The quaternary ammonium salts are used in the process in small but catalytic amounts. For example, amounts from about 0.5 to about 5.0 mole percent, based on the reactants, are suitable but amounts of from about 0.5 to about 1.0 mole percent are generally preferred. If it is desirable to generate the catalyst in situ, from about 0.75 to about 1.25 mole percent of a tertiary amine, (i.e. triethylamine) based on the reactants is suitable.

The process is conducted under alkaline conditions. Generally, the pH of the water phase is in the range of from about 10.5 to about 11.5. Such conditions can be easily achieved by conventional methods, e.g., by conducting the process in the presence of caustic or other base.

The nitrile-forming reaction proceeds at a satisfactory rate at a temperature of from about 40° C. up to about 100° C. with a preferred rate being obtained at temperatures of about 50° C. to 70° C. At 40° C., the nitrile-forming reaction may require approximately 16 hours while at 100° C., the same reaction requires approximately 30 minutes. At lower temperatures than those indicated, an overly long reaction period results; at higher temperatures, product decomposition and phase separation become problematic.

Agitation (i.e., stirring, swirling, etc.) of the reaction mixture is particularly advantageous for this process because the reactants are predominantly in different phases of the two-phase reaction medium.

Generally, the chloromethylation reaction and the nitrile-forming reaction are not pressure sensitive and atmospheric or superatmospheric pressures are used as a matter of convenience. Under the above conditions, chloromethylation reaction times of up to 4 hours are common; nitrile-forming reaction times of up to 6 hours are common and generally sufficient for the respective reactions to be substantially complete.

At the end of the nitrile-forming reaction the aqueous and organic phases are separated, the desired nitrile product is in the organic layer. Isolation of the m-trifluoromethyl benzyl nitrile product from the organic layer is achieved by distillation. The distillation is preferably carried out in a pressure range of about 1 mm to about 100 mm.

The following non-limiting examples further illustrate the invention. Unless otherwise specified, parts and percentages are by weight.

EXAMPLE 1

To 589.9 parts of 90 percent chloromethyl methyl ether (CMME) in a 5-liter round bottom flask is added 732 parts of trifluoromethyl benzene (BTF). This mixture is agitated with an air-driven stirrer. Then 592.6 parts of chlorosulfonic acid is added to the CMME-BTF mixture via a dropping funnel. The temperature of the reaction mixture is controlled at 35° C.-50° C. during the acid addition. The reaction mixture is heated at 54° C.-55° C. for four hours. In a water quench, 210 parts of water is then added to the reaction mixture with cooling. Two phases are formed; the upper phase is the organic layer containing m-trifluoromethyl benzyl chloride and the lower phase is the aqueous layer containing acid bodies. The phases are split to separate the reaction crude from the bulk of the acid bodies. The upper phase (organic layer) is treated with 1025 parts of 20 percent NaOH solution with cooling to remove bis-chloromethyl ether impurities. After stirring for one hour, at a temperature of about 50° C., the phases are again separated to remove the aqueous caustic layer from the organic reaction crude. The organic phase or product layer is charged to a flash still to remove methanol, water and part of the unreacted BTF. The remaining BTF-benzyl chloride crude is combined with 516 parts of 20 percent NaCN solution and 6 parts of 75 percent methyl tributylammonium chloride (MTBA). The mixture is stirred for approximately 14 hours at 55° C. at which point the conversion of m-trifluoromethyl benzyl chloride is >99 percent. At the end of this reaction period the aqueous and organic layers are separated and 765 parts of organic material containing the nitrile product is vacuum distilled. 310 Parts of BTF and 283 parts of m-trifluoromethyl benzyl nitrile are recovered from the distillation step. This experiment demonstrates that without isolating the benzyl chloride intermediate, the benzyl nitrile product is obtained in high yield at a commercially attractive reaction rate.

EXAMPLES 2-5

In substantially the same manner as in Example 1, undistilled or crude m-trifluoromethyl benzyl chloride is prepared and used in the nitrile-forming reactions of these examples. Various times, temperature, phase transfer catalysts, or molar ratios of sodium cyanide:m-trifluoromethyl benzyl chloride:-phasetransfer catalyst (NaCN: TFBC:PTC) are set forth in Table I below. The undistilled m-trifluoromethyl benzyl chloride product is assayed by vapor phase chromatography to accurately determine the molar quantities of TFBC reported in each ratio. The addition of the phase transfer catalyst is made at two separate intervals rather than as a single addition as reported in Example 1. It is found that a decrease in total reaction time can be achieved with lower NaCN/TFBC ratios by adding the phase transfer catalyst at two separate intervals. The second addition is made when the TFBC is about 90 percent converted; this causes the reaction to finish in a short time and requires less of the PTC agent than when making a single addition.

2.0:1.0:1.0; quenching the chloromethylation reaction product with water thereby forming an aqueous acid layer and a crude organic chloromethylation product layer; treating the crude organic chloromethylation product layer with an aqueous caustic solution to remove bis-chloromethyl ether impurities; separating the resulting aqueous caustic layer from the crude organic chloromethylation product layer which is essentially free of bis-chloromethyl ether; partially concentrating the ether-free chloromethylation reaction product by removing methanol, water and some of the unreacted trifluoromethyl benzene; and contacting the remaining undistilled chloromethylation reaction product containing m-trifluoromethyl benzyl chloride with aqueous sodium cyanide in the presence of a phase transfer catalyst to form the nitrile.

2. The process of claim 1 wherein triethylamine is reacted with the undistilled chloromethylation reaction product containing m-trifluoromethyl benzyl chloride to generate in situ m-trifluoromethyl benzyl triethyl ammonium chloride, a phase transfer catalyst.

3. The process of claim 1 wherein the phase transfer catalyst is a quaternary ammonium salt of the formula $R_1R_2R_3R_4N^{\oplus}A^{\ominus}$, wherein $R_1$-$R_4$ are each independently hydrocarbyl groups of from 1 to about 12 carbon atoms, or $R_1$ is joined with $R_2$ to form a 5- or 6-membered heterocyclic ring wherein one member of said heterocyclic ring is a quaternized nitrogen atom, a second member of said heterocyclic ring is an atom of carbon, nitrogen, oxygen or sulfur, and the remaining members of said heterocyclic ring are carbon atoms; and $A^{\ominus}$ is an anion; said quaternary ammonium salt having a minimum solubility of at least about 1 weight percent in both the organic phase and the aqueous phase of a two-phase reaction medium at 25° C.

4. The process of claim 3 wherein said quaternary ammonium salt is a methyl tributyl-, methyl trioctyl-, or methyl tridecyl-ammonium salt.

5. The process of claim 3 wherein said quaternary ammonium salt is methyl tributyl-, methyl trioctyl-, or methyl tridecyl-ammonium chloride.

6. The process of claim 3 wherein said ammonium salt

TABLE I

| Example No. | Nitrile-forming Reaction Using Undistilled m-Trifluoromethyl Benzyl Chloride | | | | |
|---|---|---|---|---|---|
| | Molar Ratio of Reactants NaCN:TFBC:PTC | Catalyst | Time | Temperature | Conversion of TFBC |
| 2 | 1.2:1.0:0.2 | methyl tri-n-butyl ammonium chloride | 7 hrs | 70° C | 94% |
| 3 | 1.2:1.0:0.2 | Adogen 464®* | 7 hrs | 70° C | 95% |
| 4 | 1.1:1.0:0.1 | methyl tri-n-butyl ammonium chloride | 24 hrs | 60° C | 99% |
| 5 | 1.1:1.0:0.1 | methyl tri-n-butyl ammonium chloride | 20 hrs | 55° C | 96% |

*Adogen 464®, a tri $C_8$-$C_{10}$ alkyl methyl chloride quaternary ammonium salt manufactured by Ashland Chemical Company, Division of Ashland Oil.

What is claimed is:

1. A process for the production of m-trifluoromethyl benzyl nitrile comprising chloromethylating trifluoromethyl benzene with chloromethyl methyl ether in the presence of chlorosulfonic acid wherein the molar ratios of chloromethyl methyl ether:chlorosulfonic acid:-trifluoromethyl benzene are from 1.2:1.0:0.5 to is present in an amount of from about 0.5 to about 5.0 mole percent, based on the combined moles of the starting reactants.

7. The process of claim 1 wherein the reaction temperature is from about 40° C. to about 100° C.

* * * * *